United States Patent [19]

Beilharz et al.

[11] Patent Number: 5,494,675
[45] Date of Patent: Feb. 27, 1996

[54] ANTI-DANDRUFF SHAMPOO

[75] Inventors: Helmut Beilharz, Shriesheim; Bernard Seubert, Edingen-Neckarhausen; Urs Riede, Freiburg St. Georgen, all of Germany

[73] Assignee: Rutgerswerke Aktiengesellschaft, Germany

[21] Appl. No.: 943,737

[22] Filed: Sep. 11, 1992

[30] Foreign Application Priority Data

Oct. 2, 1991 [DE] Germany .......................... 41 32 798.5

[51] Int. Cl.$^6$ ................................ A61K 7/00; A61K 7/06
[52] U.S. Cl. ................................ 424/401; 424/DIG. 4; 424/70.8; 514/852; 514/880; 514/881
[58] Field of Search ................ 424/70, 401, DIG. 4, 424/70.8; 514/852, 863, 864, 881, 949, 880, 770

[56] References Cited

U.S. PATENT DOCUMENTS

| | | | |
|---|---|---|---|
| 4,637,933 | 1/1987 | Zabotto neé Arribau | 514/949 |
| 4,913,898 | 4/1990 | Altobelli | 514/949 |
| 4,931,274 | 6/1990 | Barabino | 514/852 |
| 4,946,829 | 8/1990 | Seubert | 514/730 |
| 4,952,563 | 8/1990 | Seubert | 514/770 |

*Primary Examiner*—Thurman K. Page
*Assistant Examiner*—Sally Gardner
*Attorney, Agent, or Firm*—Bierman and Muserlian

[57] ABSTRACT

A method of treating dandruff in warm-blooded animals comprising applying to the hair of a warm-blooded animal an anti-dandruff effective amount of an alkali metal or ammonium salt of a low molecular weight huminate with a mean molecular weight of 1000 with a range of 300 to 1500 and a method of treating or preventing dandruff.

4 Claims, No Drawings

ANTI-DANDRUFF SHAMPOO

STATE OF THE ART

Dandruff is a wide-spread cosmetic problem, and to fight it a plurality of active substances have been proposed and employed. Probably the best and most successful anti-dandruff agent is zinc pyrithion, known from U.S. Pat. No. 3,236,733 as an ecologically and physiologically safe substance which is added to shampoo in a simple manner. It spreads on the scalp as the hair is being washed and is fixed so that an effective amount remains on the scalp after the hair wash.

However, anti-dandruff preparations or shampoos which contain pyrithion-containing compounds have the disadvantage that they stimulate the scalp to grease up again more [Cf. Seifen-Oele-Fette-Wachse, Vol. 108 (1982), p 471–475]. Attempts have been made to minimize this side effect by reducing the amount of active ingredients and by adding additional active ingredients, particularly film-forming fatty ethers, so-called re-greasers.

OBJECTS OF THE INVENTION

It is an object of the invention to provide shampoos with a good anti-dandruff activity without side effects so that the anti-dandruff treatment occurs with the washing of the hair.

It is another object of the invention to provide an improved method of treating dandruff in warm-blooded animals.

These and other objects and advantages of the invention will become obvious from the following detailed description.

THE INVENTION

The novel anti-dandruff compositions of the invention are comprised of a shampoo formulation containing as the anti-dandruff agent an anti-dandruff effective amount of an alkali metal or ammonium salt of a low molecular weight huminate with a mean molecular weight of 1000 with a range of 300 to 1500.

The alkali metal and ammonium salts of low molecular weight huminates with a mean molecular weight of 1,000 with a molecular weight average of 300 to 1500 are known. U.S. Pat. No. 4,918,059 and U.S. Pat. No. 4,946,829 teach the natural salts, and U.S. Pat. No. 4,921,840 describes their preparation by oxidation of polyvalent phenols in a weakly alkaline aqueous medium. They are dark-brown, water-soluble products known to be useful for healing wounds. It is surprising to discover that they are both keratinolytic and sebostatic at low concentrations when applied for a short time in a shampoo.

The compositions can be prepared by incorporating the said huminates into a shampoo at a concentration of 0.1 to 3% by weight and the formation of dandruff and re-greasing of the skin is suppressed when applied to the skin, particularly the scalp and hair. Moreover, the keratinocytes are stimulated in a pro-inflammatory sense.

The compositions may also contain additional cosmetically or medically active substances and may also be used as aqueous solutions alone. They can be applied to the hair and scalp with rubbing and after a contact time of 6 to 15 minutes, it can be washed out with water.

In the following example, there is described several embodiments to illustrate the invention. However, it is to be understood that the invention is not intended to be limited to the specific embodiments.

EXAMPLE 1

100 ml of a commercial shampoo were mixed with 50 ml of a 5% aqueous solution of an alkali metal huminate of low molecular weight prepared by a) Example 1 of U.S. Pat. No. 4,918,059, b) the example of U.S. Pat. No. 4,921,840 and c) Example 2 of U.S. Pat. No. 4,946,829.

Several test persons suffering from dandruff used one of the shampoos they had received for daily washing of hair and scalp twice with 5 ml of the shampoo. The results were the same in all cases. After a period of about 1 week, the dandruff problem was no longer acute. Even after using the shampoos for several weeks, an increase in sebaceous gland activity was not observable on the scalp. In some cases, a reduction of the greasing of the hair was noted subjectively.

Various modifications of the compositions and method may be made without departing from the spirit or scope therefore and it is to be understood that the invention is intended to be limited only as defined in the appended claims.

What we claim is:

1. A method of treating dandruff in warm-blooded animals comprising applying to the hair of a warm-blooded animal an anti-dandruff effective amount of an alkali metal or ammonium salt of a low molecular weight huminate with a mean molecular weight of 1000 with a range of 300 to 1500.

2. The method of claim 1 wherein the huminate is contained in a shampoo formulation at a concentration of 0.1 to 3% by weight of the shampoo.

3. An anti-dandruff shampoo formulation containing as the anti-dandruff agent an anti-dandruff effective amount of an alkali metal or ammonium salt of a low molecular weight huminate with a mean molecular weight of 1000 with a range of 300 to 1500.

4. The shampoo of claim 3 wherein the concentration of huminate is 0.1 to 3% by weight based on the shampoo.

\* \* \* \* \*